United States Patent
Johnson

(10) Patent No.: US 8,413,330 B2
(45) Date of Patent: Apr. 9, 2013

(54) LONGITUDINALLY GROUND FILE HAVING INCREASED RESISTANCE TO TORSIONAL AND CYCLIC FATIGUE FAILURE

(76) Inventor: William B. Johnson, Tulsa, OK (US)

( * ) Notice: Subject to any disclaimer, the term of this patent is extended or adjusted under 35 U.S.C. 154(b) by 1156 days.

(21) Appl. No.: 12/047,369

(22) Filed: Mar. 13, 2008

(65) Prior Publication Data

US 2009/0229129 A1 Sep. 17, 2009

(51) Int. Cl.
B23P 13/00 (2006.01)

(52) U.S. Cl.
USPC ............ 29/896.1; 433/102; 451/48; 451/149; 76/12; 76/24.5

(58) Field of Classification Search .................. 29/896.1, 29/557; 451/48, 149; 76/12–24.5; 433/102
See application file for complete search history.

(56) References Cited

U.S. PATENT DOCUMENTS

| | | | |
|---|---|---|---|
| 4,611,509 A * | 9/1986 | Matsutani | 76/24.1 |
| 4,871,312 A | 10/1989 | Heath | |
| 4,934,934 A | 6/1990 | Arpaio, Jr. et al. | |
| 5,035,617 A | 7/1991 | McSpadden | |
| 5,065,549 A | 11/1991 | Speiser et al. | |
| 5,184,926 A | 2/1993 | Hemmings | |
| 5,464,362 A | 11/1995 | Heath et al. | |
| 5,527,205 A * | 6/1996 | Heath et al. | 451/48 |
| 5,628,674 A | 5/1997 | Heath et al. | |
| 5,653,590 A | 8/1997 | Heath et al. | |
| 5,655,950 A * | 8/1997 | Heath et al. | 451/48 |
| 5,735,689 A | 4/1998 | McSpadden | |
| 5,735,690 A | 4/1998 | Malentacca | |
| 5,984,679 A | 11/1999 | Farzin-Nia et al. | |
| 6,149,501 A | 11/2000 | Farzin-Nia et al. | |
| 6,299,445 B1 * | 10/2001 | Garman | 433/102 |
| 7,018,143 B2 | 3/2006 | Moore | |
| 7,018,205 B2 | 3/2006 | Abel | |
| 7,201,543 B2 * | 4/2007 | Muhlfriedel et al. | 408/230 |
| 7,789,730 B2 * | 9/2010 | Matsutani | 451/8 |
| 2004/0219484 A1 * | 11/2004 | Scianamblo | 433/102 |
| 2006/0014480 A1 | 1/2006 | Aloise et al. | |
| 2006/0265858 A1 | 11/2006 | McSpadden | |

OTHER PUBLICATIONS

Extended European Search Report issued by the European Patent Office on Jul. 9, 2009 in corresponding appln. 09250717.7.

* cited by examiner

*Primary Examiner* — Peter DungBa Vo
*Assistant Examiner* — Azm Parvez
(74) *Attorney, Agent, or Firm* — Gable Gotwals

(57) ABSTRACT

A method of producing an endodontic file that involves grinding in a plane substantially parallel to the longitudinal axis of a rotating dental instrument blank. By grinding the dental instrument blank in this manner, the torsional strength of the resulting endodontic file is not eroded during its production, thereby providing a file that is less susceptible to breakage during its use.

7 Claims, 8 Drawing Sheets

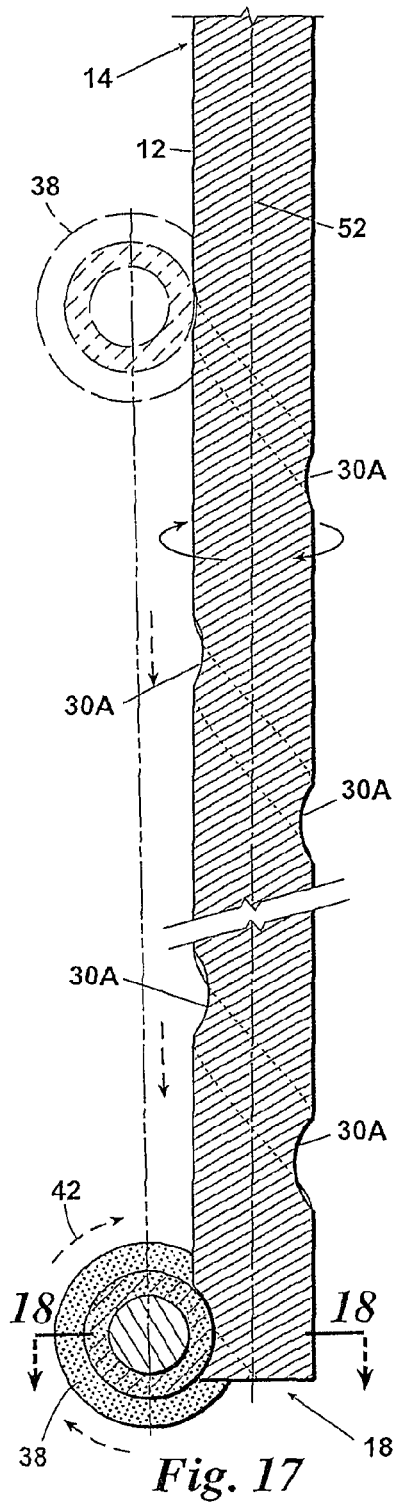
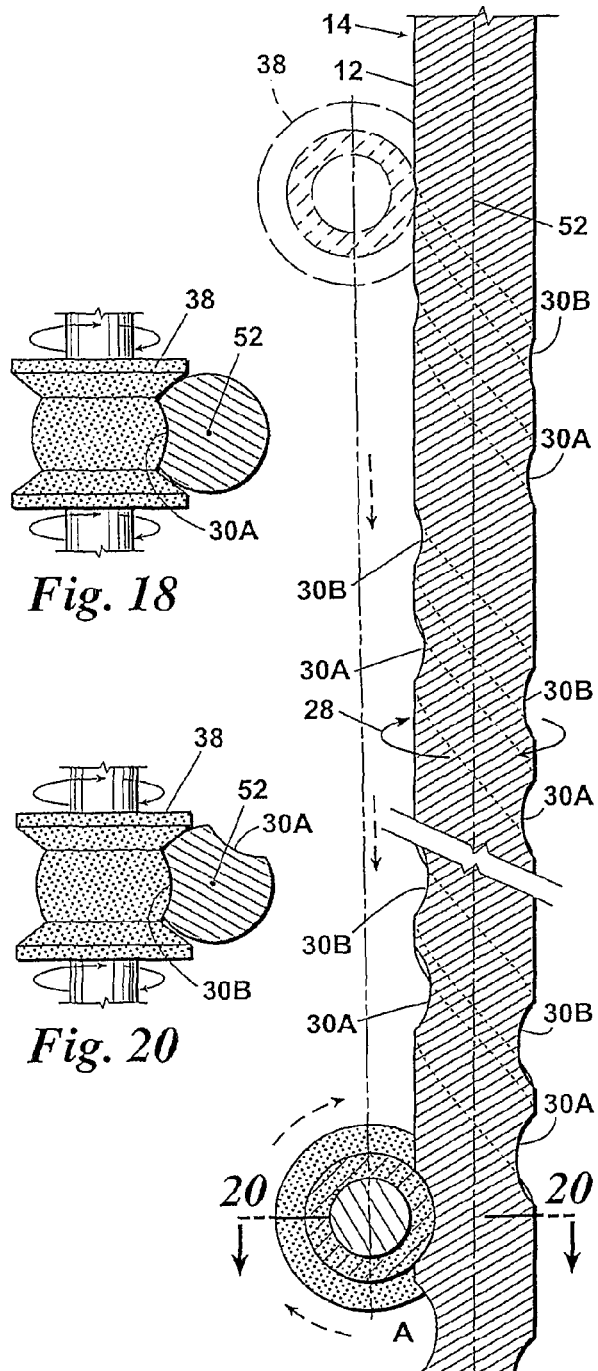
Fig. 17
Fig. 18
Fig. 20
Fig. 19

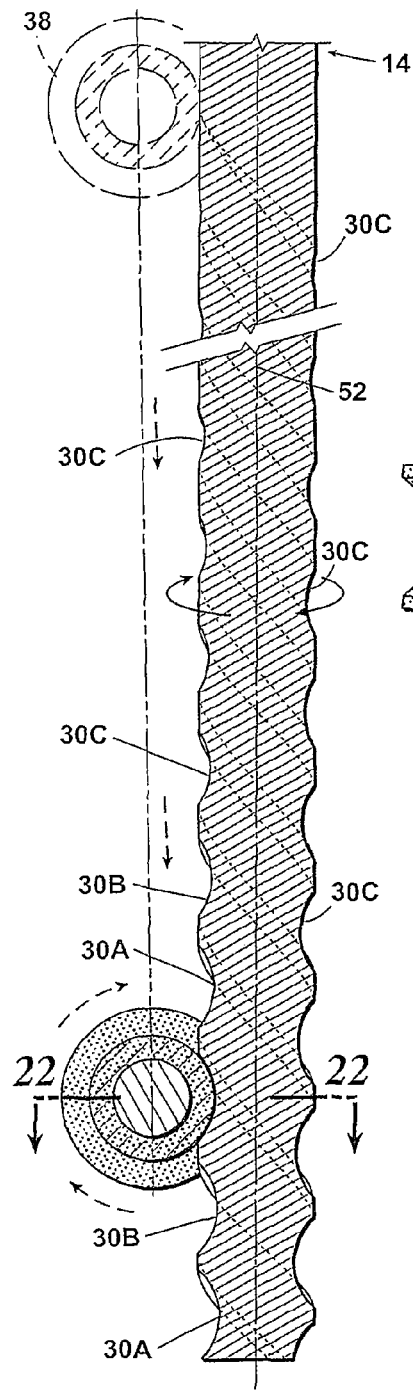
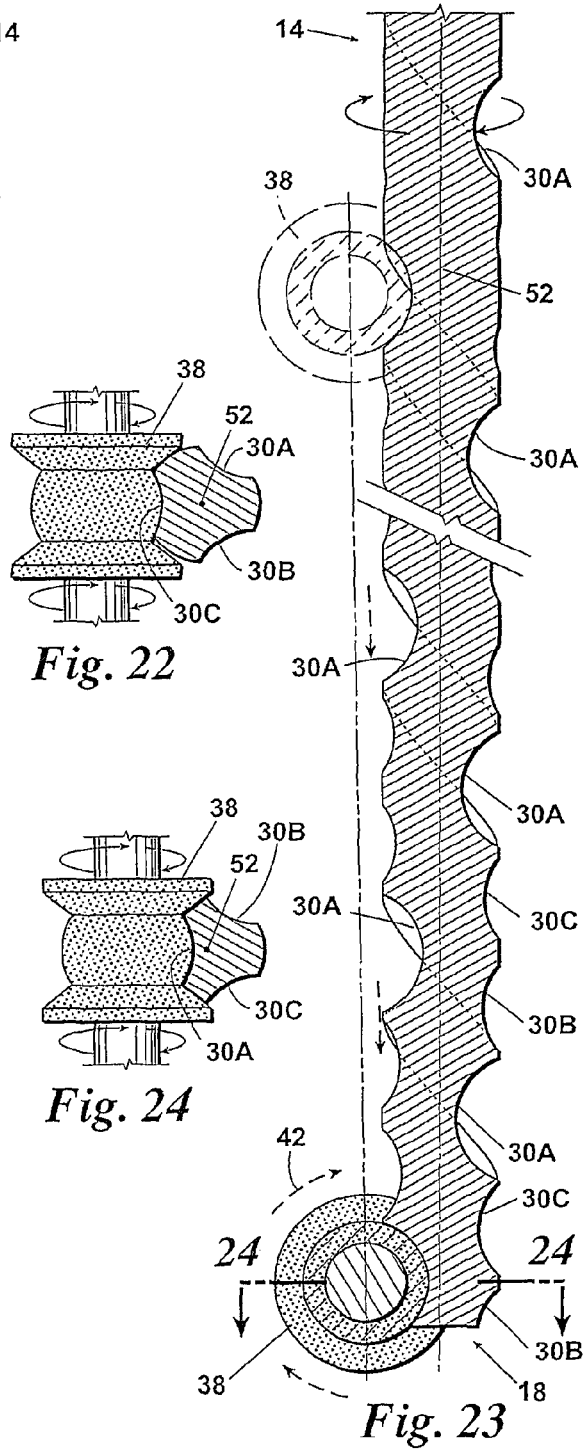
Fig. 21  Fig. 22  Fig. 23  Fig. 24

ND FILE HAVING
LONGITUDINALLY GROUND FILE HAVING INCREASED RESISTANCE TO TORSIONAL AND CYCLIC FATIGUE FAILURE

REFERENCE TO PENDING APPLICATIONS

This application is not based upon any pending domestic or international patent applications.

REFERENCE TO MICROFICHE APPENDIX

This application is not referenced in any microfiche appendix.

BACKGROUND OF THE INVENTION

1. Field of the Invention

This invention relates generally to the field of dentistry and more particularly to endodontic instruments used for cleaning and enlarging a root canal of a tooth.

| U.S. Pat. No. | Inventor | Title |
|---|---|---|
| 4,871,312 | Heath | Dental Compactor Instrument |
| 4,934,934 | Arpaio, Jr. et al. | Dental File/Reamer Instrument |
| 5,035,617 | McSpadden | Endodontic Instrument |
| 5,065,549 | Speiser et al. | Method and Apparatus For Manufacturing K-Files and Reamers |
| 5,184,926 | Hemmings | Root-Strength Drill Bit and Method of Making |
| 5,628,674 | Heath et al. | Endodontic Instrument |
| 5,653,590 | Heath et al. | Kit of Endodontic Instruments and Method of Utilizing Same |
| 5,735,689 | McSpadden | Endodontic Dental Instrument |
| 5,735,690 | Malentacca | Set of Drills For The Boring Of The Coronary Part of Dental Radicular Canals |
| 6,149,501 | Farzin-Nia et al. | Superelastic Endodontic Instrument, Method of Manufacture, and Apparatus Therefor |
| 6,299,445 | Garman | Endodontic Instrument, Instrument Blank and Method of Manufacture |
| 7,018,143 | Moore | Reduced Energy Consuming, Lateral Cutting Twist Drill |
| 7,018,205 | Abel | Barbed Endodontic Instrument |
| 2004/0,219,484 | Scianamblo | Endodontic Instrument Having Reversed Helix |
| 2006/0,014,480 | Aloise et al. | Method of Manufacturing A Dental Instrument |
| 2006/0,265,858 | McSpadden | Endodontic Instrument Having Notched Cutting Surfaces |

2. Description of the Related Art

Instruments that enable an endodontist to clear and clean the canal of a tooth are well-known in the art. These instruments, typically referred to as endodontic files, experience significant flexing and twisting while in use, making them susceptible to breakage. Because of the breakage problem and the danger that it poses to a patient, nickel-titanium alloy (NiTi or Nitinol™) generally is viewed as a better material for use in manufacturing these instruments than is stainless steel. Relative to stainless steel, NiTi is able to withstand a far greater amount of twisting or bending without experiencing permanent deformation or breaking.

The manufacturing methods typically used for producing stainless steel instruments have proven themselves unsatisfactory when applied to NiTi. These methods include (1) twisting a prismatic rod having a square or triangular cross section to create a file with a fluted cutting edge and (2) grinding helical flutes along the length of a circular or tapered rod to create a file with one or more helical cutting surfaces. Twisting cannot be used because of the superelastic property of NiTi and traditional grinding methods leave areas of stress having radial planar components that reduce the torsional resistance of a file.

Methods of manufacturing specifically designed for NiTi provide a clean cutting edge but involve grinding or hacking methods that reduce the torsional strength of the file by creating stress areas lying perpendicular to the longitudinal axis of the file. The same is true of the traditional grinding and hacking methods used to form a file made of stainless steel. Breakage of the file due to torsion usually occurs in one or more of these cross-sectional areas. Additionally, currently available methods of grinding NiTi for use as an endodontic file are relatively expensive and slow. Therefore, a need exists for a method of manufacturing an endodontic file made of stainless steel or NiTi—or other materials that exhibit the desired superelastic properties of NiTi—that does not erode the torsional strength of the file. None of the prior art alone or in combination meets this need or renders the present invention obvious.

For background information relating to instruments of the type that is the subject of this patent application, reference may be had to the following issued United States patents and publications:

BRIEF SUMMARY OF THE INVENTION

The invention herein relates to a method of producing a dental instrument, commonly referred to as an endodontic file. The endodontic file produced has one or more flutes continuously spiraled over its working length, and the file can be cylindrical-shaped or tapered and cylindrical-shaped. The method involves feeding a rotating dental instrument blank past a rotating grinding wheel so that all grinding is done in a plane substantially parallel to that of the longitudinal axis of the dental instrument blank. By grinding the blank in a plane parallel to its longitudinal axis, the torsional strength of the blank is not eroded during the method of producing the endodontic file. The blank also can be advanced past the grinding wheel at a feed rate that corresponds to a distance that the blank rotates in a single revolution. The rotational axis of the grinding wheel can be positioned relative to a tapered dental instrument blank so as to maintain a selected depth-of-grind over the working length of the blank as a helical-shaped flute is ground.

This invention also includes an apparatus for producing an endodontic file according to the above method. The apparatus includes a gripping fixture to which the dental instrument blank is secured during grinding. The gripping fixture helps to move the dental instrument blank in a linear path past the grinding wheel as the fixture rotates the blank about its longitudinal axis. The rotation of the blank is indexed to the displacement of the gripping fixture so that all grinding takes place in a plane substantially parallel to the longitudinal axis of the blank.

A better understanding of the invention will be obtained from the following detailed description of the preferred embodiments and claims, taken in conjunction with the attached drawings.

BRIEF DESCRIPTION OF THE DRAWINGS

FIG. 17 is a cross-sectional view of the rod after its first pass past the grinding wheel.

FIG. 18 is a cross-sectional view of the rod taken along section line 18-18 of FIG. 17.

FIG. 19 is a cross-sectional view of the rod after a first pass past the grinding wheel to form a second-helical shaped groove along a surface of the rod.

FIG. 20 is a cross-sectional view of the rod taken along section line 20-20 of FIG. 19.

FIG. 21 is a cross-sectional view of the rod after a first pass past the grinding wheel to form a third-helical shaped groove along a surface of the rod.

FIG. 22 is a cross-sectional view of the rod taken along section line 22-22 of FIG. 21.

FIG. 23 is cross-sectional view of the rod after a second pass past the grinding wheel to complete a first helical-shaped groove along a surface of the rod.

FIG. 24 is a cross-sectional view of the rod taken along section line 24-24 of FIG. 23.

DETAILED DESCRIPTION OF THE PREFERRED EMBODIMENTS

Figures 1, 2:
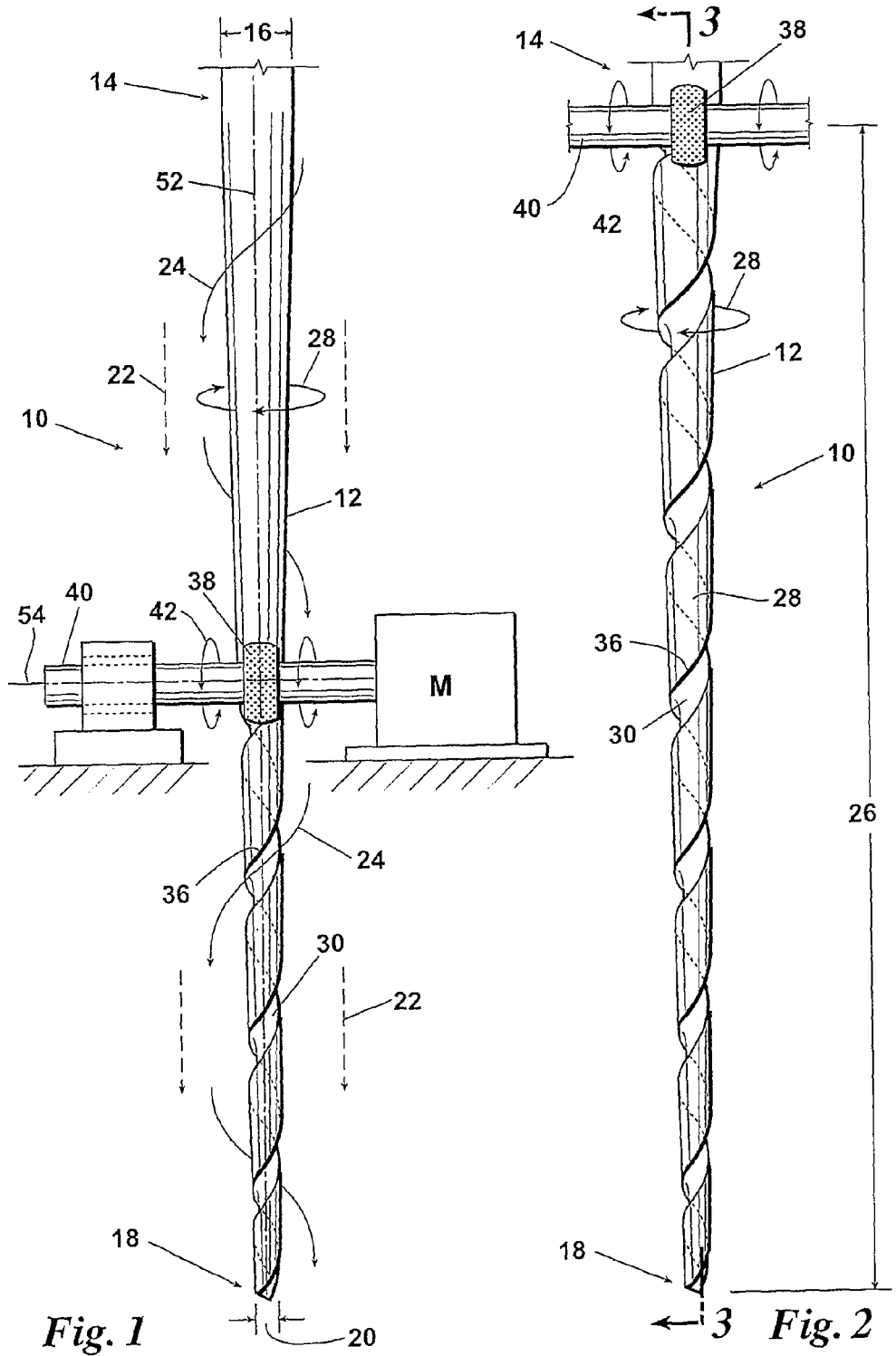
FIG. 1 is a view of a dental instrument blank in the form of a tapered, cylindrical-shaped rod as it is rotated about and advanced along its length in contact with a grinding wheel. The grinding wheel is oriented perpendicular to a rotational axis of the wheel. As the rod is moved past the wheel, the wheel cuts a first flute along a surface of the rod. All grinding takes place in a plane substantially parallel to a longitudinal axis of the rod.
FIG. 2 is a view of the rod after the grinding wheel has completed cutting the first flute.

It is to be understood that the invention that is now to be described is not limited in its application to the details of the construction and arrangement of the parts illustrated in the accompanying drawings. The invention is capable of other embodiments and of being practiced or carried out in a variety of ways. The phraseology and terminology employed herein are for purposes of description and not limitation.

Elements illustrated in the drawings are identified by the following numbers:

| | |
|---|---|
| 10 | Endodontic file |
| 12 | Rod |
| 14 | Shank end |
| 16 | Shank end diameter |
| 18 | Distal end |
| 20 | Distal end diameter |
| 22 | Linear travel path of the blank |
| 24 | Helical-shaped travel path |
| 26 | Working length |
| 28 | Rod rotation |
| 30A | First flute |
| 30B | Second flute |
| 30C | Third flute |
| 36 | Helical land |
| 38 | Grinding wheel |
| 40 | Spindle |
| 42 | Spindle rotation |
| 44 | Handle |
| 46 | Shank portion |
| 48 | Calibrated depth markings |
| 50 | File portion |
| 52 | Longitudinal axis of the rod |
| 54 | Longitudinal axis of the spindle |
| 58 | Relative travel path of the wheel |

Referring to the drawings and first to FIGS. 1 and 2, a dental instrument blank in the form of rod 12 with a shank end 14 and a distal end 18 is secured at the shank end 14 to a gripping fixture (not shown). The gripping fixture is of a type well-known in the art and is capable of moving rod 12 in a linear travel path 22 past and in contact with a fine-grit grinding wheel 38 while simultaneously rotating rod 12 about a longitudinal axis 52 of the rod 12. The combination of linear travel path 22 and rotation 28 produces a helical-shaped travel path 24 along the working length 18 of rod 12 as rod 12 moves past grinding wheel 38.

The rod 12 is of a type, size, and geometry well-known in the art for producing an endodontic file 10, and is typically cylindrical-shaped or tapered and cylindrical. The shank end diameter 16 and distal end diameter 20 of the rod 12 closely conform to a desired shank end diameter 16 and a desired distal end diameter 20 of the endodontic file 10 to be produced. The diameter of rod 12 might also closely conform to the shank end diameter 16 of the endodontic file 10 and then be ground along the working length 26 of rod 12 to produce a desired taper and distal end diameter 20.

The rotation 28 of rod 12 is indexed to the linear displacement of the gripping fixture (not shown) relative to grinding wheel 38 in order to create the spiral-shaped travel path 24 necessary to produce a desired continuous helical configuration in the form of a flute 30A along a surface of rod 12 and throughout the working length 26 of rod 12. In cases in which the endodontic instrument 10 to be produced is to be tapered along its working length 26, the gripping fixture that holds rod 12 is angled relative to the geometry of the grinding wheel 38 so as to control and vary depth-of-grind along the working length 26 of rod 12. Grinding wheel 38 may also be angled relative to the geometry of rod 12.

Figure 3:
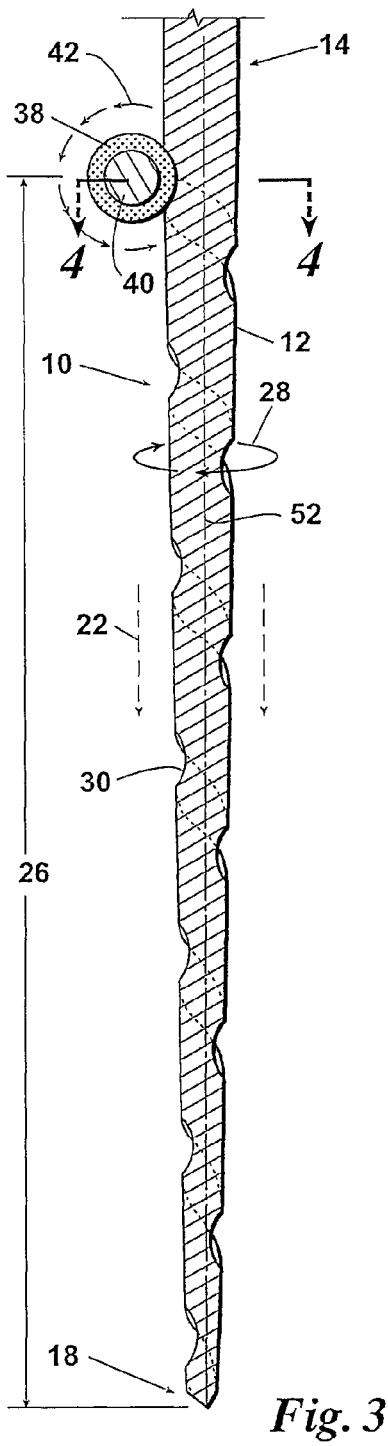
FIG. 3 is a cross-sectional view of the rod taken along section line 3-3 of FIG. 2 and showing a profile of the first flute and the grinding wheel.
Figure 4:
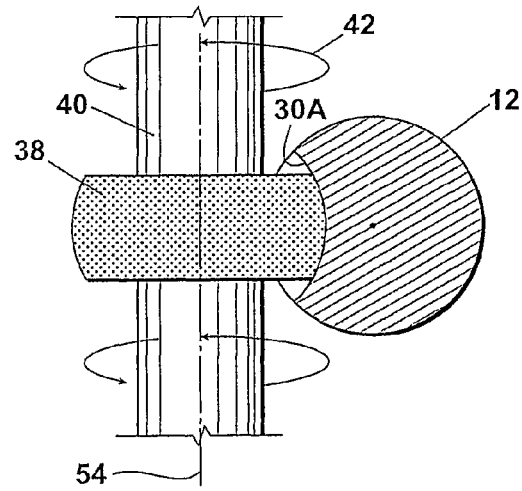
FIG. 4 is a cross-sectional view of the rod taken along section line 4-4 of FIG. 3.

The grinding wheel 38 is mounted on a spindle 40 of a standard grinding machine M. Grinding wheel 38 is oriented on the spindle 40 so that the grinding wheel 38 rotates about a longitudinal axis 54 of spindle 40 that is substantially perpendicular to the longitudinal axis 52 of the linearly advancing and rotating rod 12. This arrangement produces rotation of the grinding wheel 38 that is in a plane substantially parallel to the longitudinal axis 52 of rod 12. As illustrated by FIG. 3, all grinding on the surface of rod 12 takes place in a plane substantially parallel to the longitudinal axis 52 of the rod 12. Because grinding of flute 30A is being done in a plane substantially parallel to—and not perpendicular to—the longitudinal axis 52 of rod 12, the torsional strength of endodontic file 10 is not eroded. As illustrated by FIG. 4, the curved-shaped geometry of the cutting surface of grinding wheel 38—in combination with the appropriate rate and depth of helical-shaped travel 24—produces the desired geometry of the flute 30A.

The feed rate of rod 12 past grinding wheel 38, speed of grinding wheel 38, and depth-of-grind of grinding wheel 38 may be sufficient to remove in a single pass the amount of material required to produce the desired geometry of flute 30A, or multiple passes may be employed with grinding wheel 38 set at a successively lower depth-of grind. In cases in which a single pass is used, working length 26 of rod 12 is moved past grinding wheel 38 a number of times equal to the number of flutes required for the endodontic file 10. Between each successive pass of rod 12 past grinding wheel 38, rod 12 is indexed by the gripping fixture so as to present a non-ground surface of rod 12 for grinding the next flute 30. For an endodontic instrument having three flutes, 30A, 30B, 30C, rod 12 would be indexed 120° between successive passes past grinding wheel 38.

Figure 7:
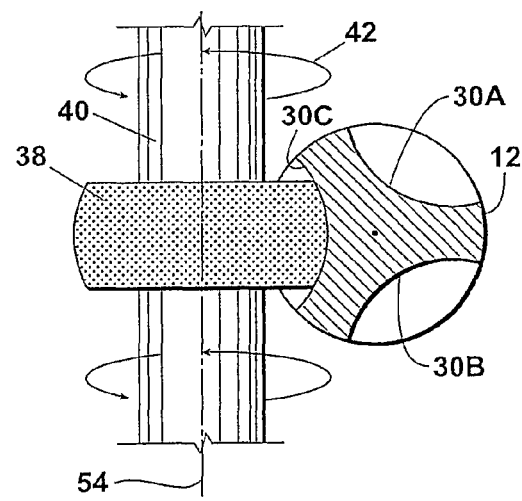
FIG. 7 is a cross-sectional view of the rod taken along section line 7-7 of FIG. 6.
Figure 5:
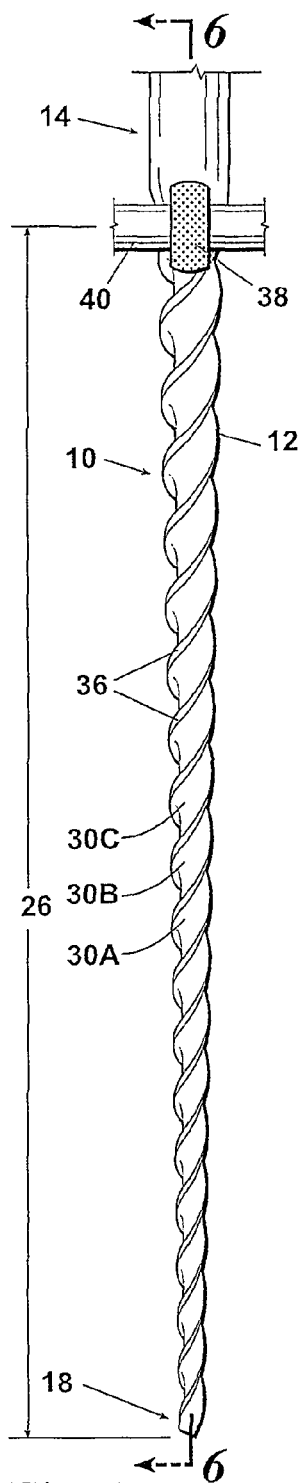
FIG. 5 is a view of the rod after the grinding wheel has completed cutting a third flute.
Figure 6:
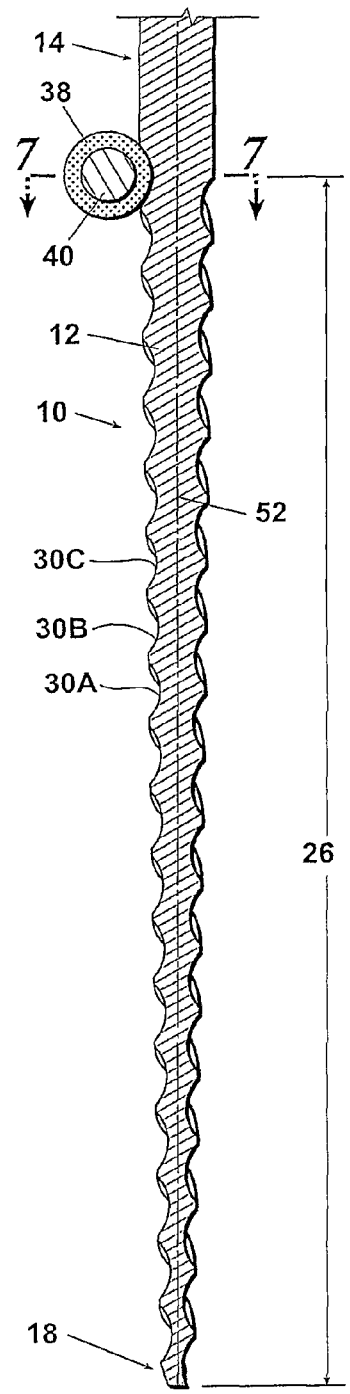
FIG. 6 is a cross-sectional view of the rod taken along section line 6-6 of FIG. 5 and showing a profile of the rod and the grinding wheel after the grinding wheel has completed cutting the third flute.

As illustrated by FIGS. 5 to 7, a first, second, and third pass of rod 12 past grinding wheel 38 produces the first flute 30A, a second flute 30B, and third flute 30C, respectively. Each flute 30A, 30B, and 30C has a substantially similar geometry and continuous helical configuration along the working length 26 of rod 12. The grinding of rod 12 that produces flutes 30A, 30B, and 30C also forms a helical land 36 on the outer periphery of rod 12. Helical land 36 is continuous along the working length of the rod 12 and is located between adjacent flutes.

Figure 8:
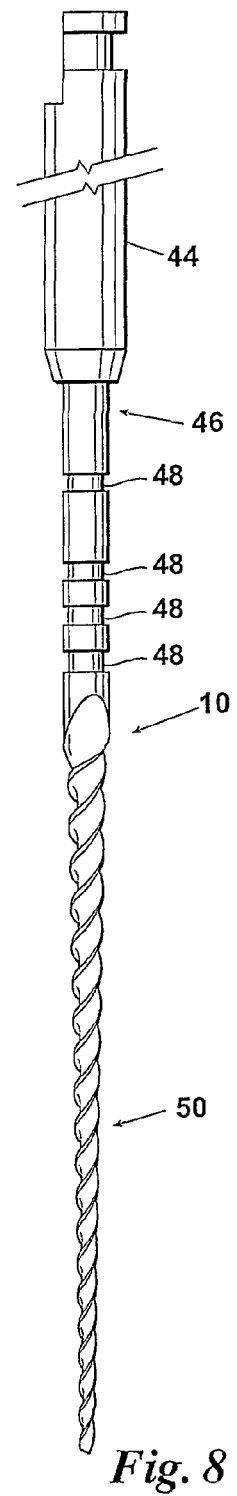
FIG. 8 is a view of a finished endodontic file.

FIG. 8 illustrates an endodontic file 10 produced by the method described above. The file 10 comprises a handle 44, a shank portion 46 having calibrated depth markings 48, and a file portion 50.

In a preferred embodiment, a file blank 12 is used, having a circular cross-section and composed of NiTi, a working length 26, a shank end diameter 16, a distal end diameter 20 of, and a degree of taper along its working length 26, all in accord with the specification of the file 10 being manufactured. The gripping fixture is angled relative to vertical so as to control and vary the depth-of-grind in the peripheral surface of rod 12 along its working length 26. Rod 12 is rotated 28 about its longitudinal axis 52 and moved in a linear travel path 22 past a rotating grinding wheel 38. Grinding wheel 38 is substantially convex-shaped and oriented so that all grinding takes place in a plane substantially parallel to the longitudinal axis 52 of rod 12. The combination of rotation 28 and linear advancement of the rod 12 past the grinding wheel 38 produces a continuous helical configuration 28 in rod 12. Because all grinding is in a plane substantially parallel to the longitudinal axis 52 of rod 12, creation of stress areas having radial planer components in rod 12 are eliminated or at least substantially reduced. That is, grinding is accomplished in a manner to reduce the creation of torsional stress weakness in finished file 10. A total of three passes are used to create a final endodontic instrument 10 having three continuous flutes 30A, 30B, and 30C and associated helical lands 36.

Figure 9:
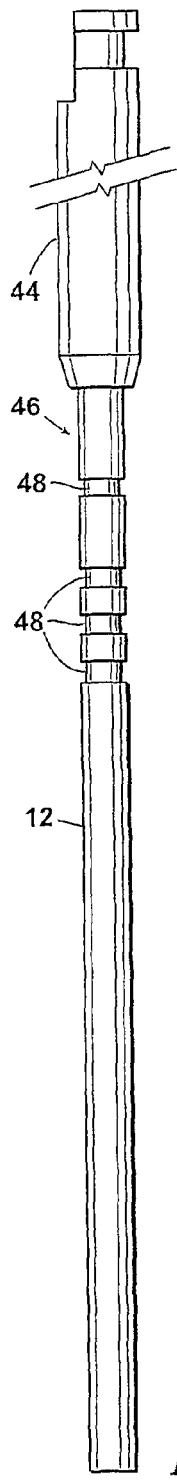
FIG. 9 is a view of a dental instrument blank in the form of a cylindrical-shaped, non-tapered dental instrument rod prior to grinding a taper and a flute along a surface of the rod.
Figure 10:
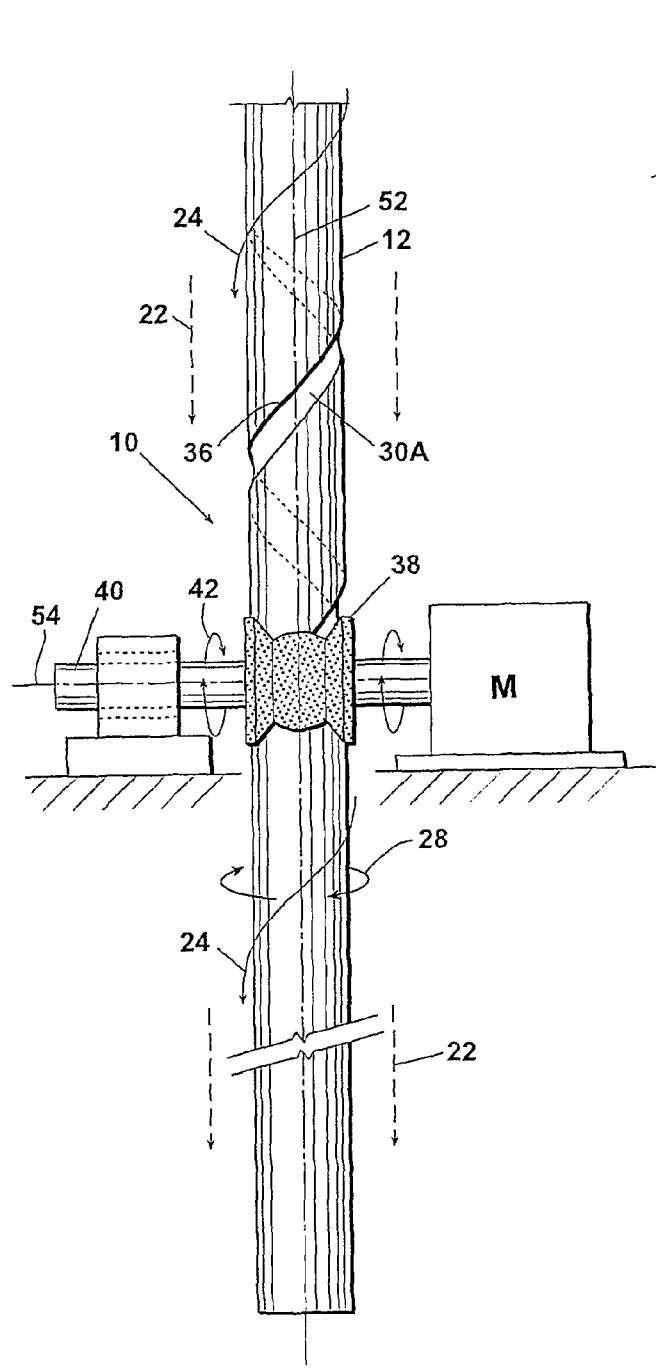
FIG. 10 is a view of the rod as the grinding wheel cuts a first flute in the rod. The rod is rotated about a longitudinal axis of the rod and advanced along its length in contact with a grinding wheel. The grinding wheel is oriented perpendicular to a rotational axis of the grinding wheel. The relative path of the wheel follows a slight angle relative to the longitudinal axis of the rod and all grinding takes place in a plane substantially parallel to the longitudinal axis of the rod. The shape of the wheel and the slight angle produces the flute and a taper as a surface of the rod comes into contact with and moves past the wheel.
Figure 11:
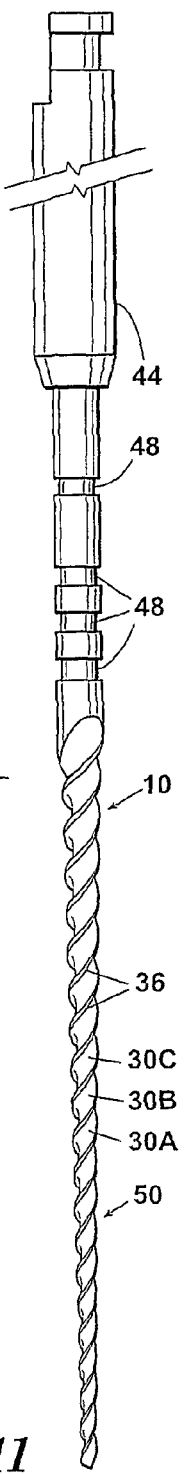
FIG. 11 is a view of the finished endodontic file.
Figure 12:
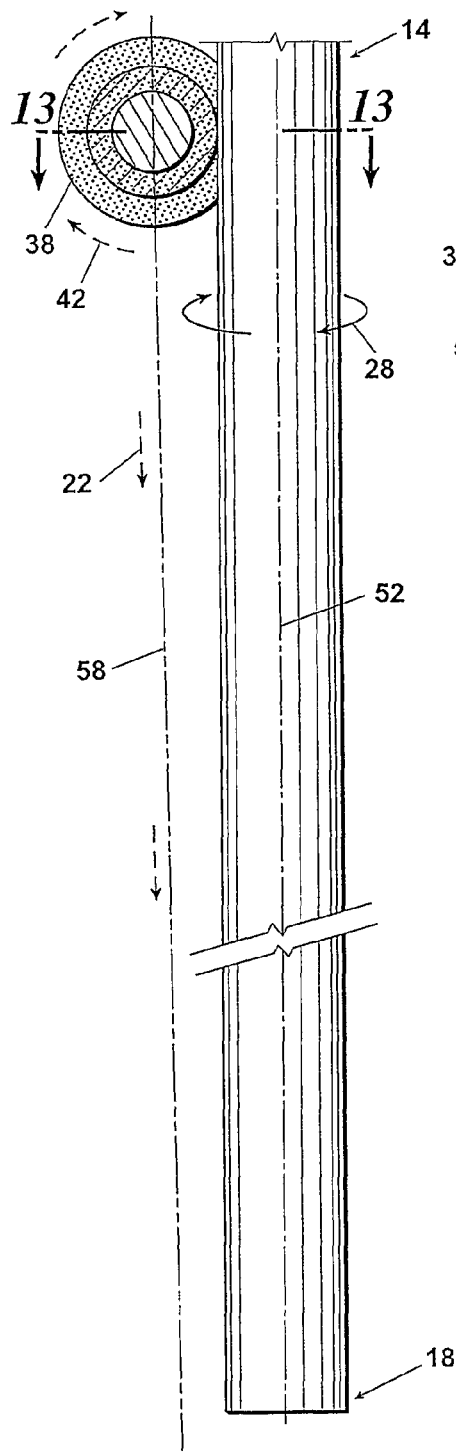
FIG. 12 is a view of the cylindrical-shaped rod as grinding begins. The rod is rotated about its cylindrical axis and the relative path of the wheel is at a slight angle to the longitudinal axis of the rod.
Figure 13:
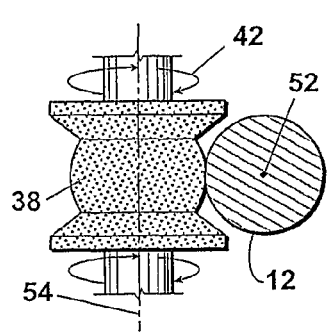
FIG. 13 is a cross-sectional view of the rod taken along section line 13-13 of FIG. 12.
Figure 15:
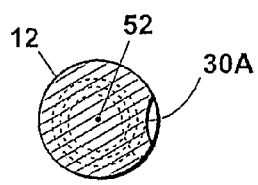
FIG. 15 is a cross-sectional view of the rod taken along section line 15-15 of FIG. 14 and showing the taper of the rod toward a distal end of the rod.
Figure 16:
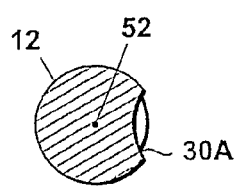
FIG. 16 is a cross-sectional view of the rod taken along section line 16-16 of FIG. 14.
Figure 14:
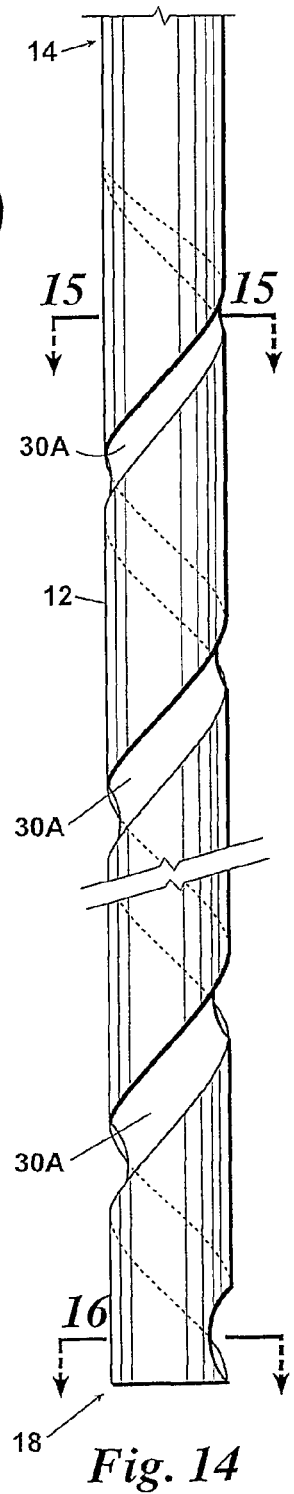
FIG. 14 is a view of the rod after a first pass past the grinding wheel to form a first helical-shaped groove along a surface of the rod.
Figure 25:
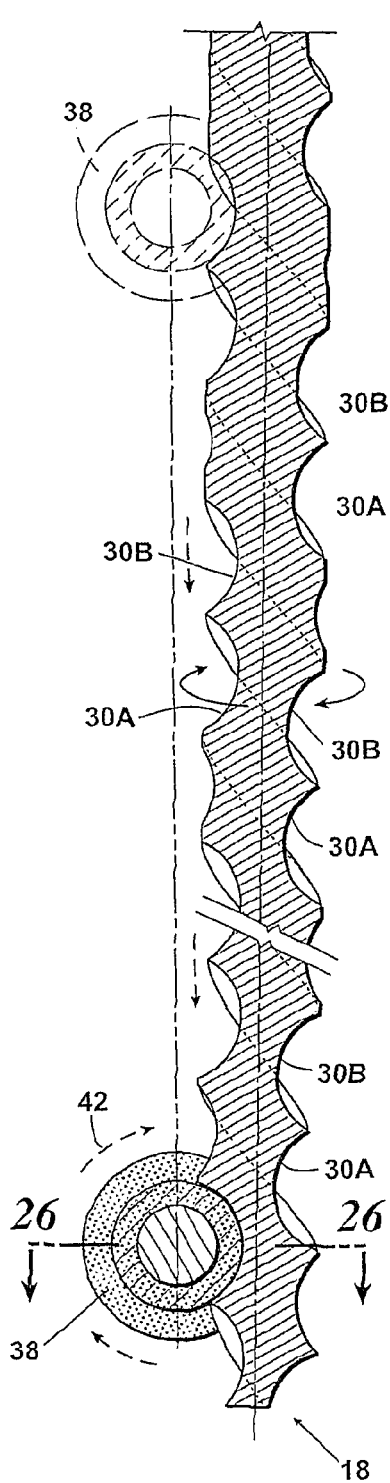
FIG. 25 is cross-sectional view of the rod after a second pass past the grinding wheel to complete a second helical-shaped groove along a surface of the rod.
Figure 26:
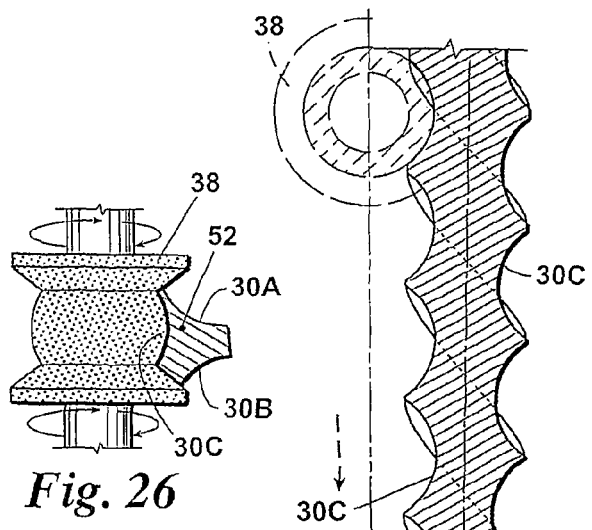
FIG. 26 is a cross-sectional view of the rod taken along section line 26-26 of FIG. 25.
Figure 27:
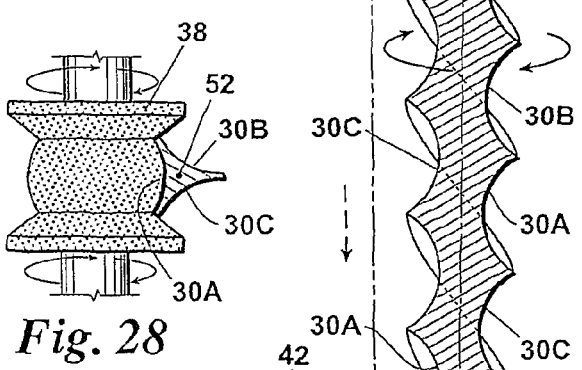
FIG. 27 is cross-sectional view of the rod after a second pass past the grinding wheel to complete a third helical-shaped groove along a surface of the rod.
Figure 28:
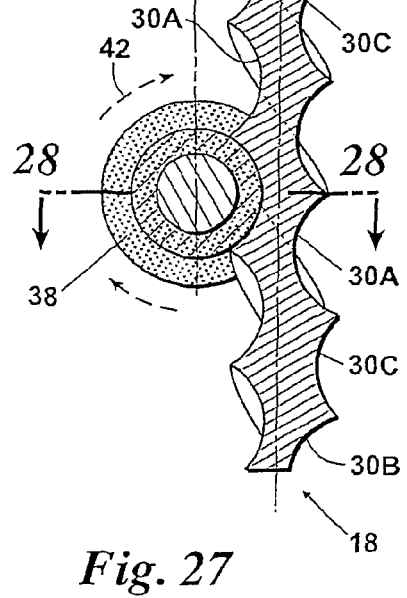
FIG. 28 is a cross-sectional view of the rod taken along section line 28-28 of FIG. 27.

Referring now to FIGS. 9 to 11, in another preferred embodiment a substantially concave-shaped grinding wheel 38 is used to simultaneously form a taper and the helical-shaped flutes 30A, 30B, and 30C. A dental instrument blank in the form of a cylindrical-shaped rod 12 is rotated about its longitudinal axis 52 and moved in a linear direction 22 past grinding wheel 38 in order to create a helical-shaped travel path 24 along a surface of rod 12. As rod 12 rotates and linearly advances helical-shaped flutes 30A, 30B, 30C are formed.

As illustrated by FIGS. 12 to 17, the travel 58 of grinding wheel 38 relative to the geometry of rod 12 follows a slight angle so that a desired degree of taper is achieved. Alternatively, the gripping fixture (not shown) may be angled relative to grinding wheel 38. In a first pass, a groove to form helical-shaped flute 30A is ground along a surface of rod 12. Depth-of-grind of flute 30A increases toward the distal end 18 of rod 12. As illustrated by FIGS. 19 to 22, rod 12 is then moved past grinding wheel 38 a second and third time to grind helical-shaped grooves forming flutes 30B and 30C, respectively. Similar to flute 30A, depth-of-grind of flute 30B, 30C increases toward the distal end 18 of rod 12. As illustrated by FIGS. 23 to 28, a fourth, fifth, and sixth pass completes flutes 30A, 30B, and 30C, respectively, to completely form flutes 30, 32, and 34. The finished endodontic file 10 has the desired taper and flute configuration.

While the invention has been described with a certain degree of particularity, many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of producing a longitudinally ground file having increased resistance to torsional and cyclic fatigue failure, the method comprising the steps of:
    providing a grinding wheel having a first rotational axis and a flute-forming peripheral surface;
    rotating the grinding wheel about the first rotational axis; and
    feeding a rotating dental instrument blank having a longitudinal axis past the rotating grinding wheel so as to grind a spiraled flute in the rotating dental instrument blank wherein the first rotational axis is perpendicular to the longitudinal axis of the blank and remains so during the feeding step.

2. A method according to claim 1 wherein the rotating dental instrument blank is tapered.

3. A method according to claim 1 wherein the rotating dental instrument blank is cylindrical-shaped.

4. A method according to claim 3 wherein the grinding wheel further comprises a taper-forming peripheral surface.

5. A method according to claim 4 wherein said feeding step comprises grinding a pre-determined taper in the rotating dental instrument blank as the spiraled flute is ground.

6. A method according to claim 1 wherein said feeding step feeds the rotating dental instrument blank at a lead which corresponds to a distance the rotating dental instrument blank travels in a single revolution thereof.

7. A method according to claim 1 further comprising the step of selectably positioning the rotational axis of the grinding wheel relative to the rotating dental instrument blank in accordance with the feed of the rotating dental instrument blank to maintain a selected depth-of-grind of the spiraled flute.

* * * * *